(12) United States Patent
Richmond

(10) Patent No.: US 9,758,817 B2
(45) Date of Patent: Sep. 12, 2017

(54) METHOD FOR IDENTIFYING A NUCLEIC ACID IN A SAMPLE

(75) Inventor: Gregory Richmond, Campbell, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 2168 days.

(21) Appl. No.: 12/687,060

(22) Filed: Jan. 13, 2010

(65) Prior Publication Data

US 2011/0171651 A1   Jul. 14, 2011

(51) Int. Cl.
 *C12Q 1/68*   (2006.01)

(52) U.S. Cl.
 CPC ......... *C12Q 1/6853* (2013.01); *C12Q 1/6844* (2013.01)

(58) Field of Classification Search
 None
 See application file for complete search history.

(56) References Cited

U.S. PATENT DOCUMENTS

| | | | |
|---|---|---|---|
| 7,422,850 B2 * | 9/2008 | Marshall et al. | 435/6.12 |
| 7,445,898 B2 | 11/2008 | Li et al. | |
| 2003/0190634 A1 * | 10/2003 | Barany et al. | 435/6 |
| 2005/0196786 A1 | 9/2005 | Levy | |
| 2008/0113875 A1 | 5/2008 | Chaurand et al. | |

FOREIGN PATENT DOCUMENTS

| | | |
|---|---|---|
| WO | WO9820166 A2 | 5/1998 |
| WO | WO2006073436 A2 | 7/2006 |

OTHER PUBLICATIONS

Xiao, M. et al. Direct determination of haplotypes from single DNA molecules. Nature Methods, vol. 6, No. 3, p. 199-201, Mar. 2009.*
Null, A.P. et al. Preparation of single-stranded PCR products fro eletrospray ionization mass spectrometry using DNA repair enzyme lambda exonuclease. Analyst, 2000, vol. 125, p. 619-626, 2000.*
Csitkovits, V. C. et al. Extent of single-stranded DNA required for efficient TraI helicase activity in Vitro. The Journal of Biological Chemistry, vol. 278 (49), p. 48696-48703, 2003.*
Ho-Pun-Cheung, A. et al. Detection of single nucleotide polymorphisms by minisequencing on a polypyrrole DNA chip designed for medical diagnosis. Laboratory Investigation, vol. 86, p. 304-313, 2006.*
Briese, T., et al. Diagnostic system for rapid and sensitive differential detection of pathogens. Emerging Infectious Diseases. 2005, vol. 11, No. 2, pp. 310-313.
Dominguez, S., et al. Multiplex MassTag-PCR for respiratory pathogens in pediatric nasopharyngeal washes negative by conventional diagnostic testing shows a high prevalence of viruses belonging to a newly recognized rhinovirus clade. Journal of Clinical Virology. 2008, vol. 43, pp. 219-222.
High-throughput SNP genotyping using Masscode technology. Qiagen News. 2001, Issue No. 2. QIAGEN Genomics, Inc., Bothell, WA.

* cited by examiner

*Primary Examiner* — Prabha Chunduru

(57) ABSTRACT

A method of sample analysis is provided. In certain embodiments, the method may comprise: contacting a nucleic acid sample with a first primer and a second primer under PCR conditions to produce a double stranded product, wherein the second primer comprises a first label and is 5' blocked; b) contacting the double stranded product with an exonuclease to degrade one strand of the double-stranded product to produce a single stranded product; c) contacting the single stranded product with a third primer under primer extension conditions, wherein the third primer comprises a second label; and d) detecting the first and second labels of the partial duplex. A kit for practicing the method is also provided.

16 Claims, 2 Drawing Sheets

METHOD FOR IDENTIFYING A NUCLEIC ACID IN A SAMPLE

BACKGROUND

Methods for identifying a nucleic acid in a sample are of great importance in clinical diagnosis, public health, veterinary health, biodefense, environmental science, and agriculture. For example, a particular pathogen in a sample can be identified and classified on the basis of its shape, growth characteristics, nutrient requirements, metabolic activity, presence of certain genes, expression of certain genes, etc. However, the process for separating and identifying pathogens is largely dominated by 19th century procedures of growing and isolating pure cultures. This is a slow and tedious process that works only for a small fraction of pathogens. Moreover, there are many pathogens that still cannot be isolated and identified in this manner.

There is a constant demand in the art for methods to identify nucleic acids in a sample. Certain aspects of this disclosure relate to such methods.

SUMMARY

A method of sample analysis is provided. In certain embodiments, the method may comprise: contacting a nucleic acid sample with a first primer and a second primer under PCR conditions to produce a double stranded product, wherein the second primer comprises a first label and is 5' blocked; b) contacting the double stranded product with an exonuclease to degrade one strand of the double-stranded product to produce a single stranded product, wherein the strand that is degraded is an extension product of the first primer; c) contacting the single stranded product with a third primer under primer extension conditions, wherein the third primer comprises a second label and wherein the contacting results in hybridization of the third primer to the single stranded product and extension thereof using the single stranded product as a template to produce a partial duplex; and d) detecting the first and second labels of the partial duplex. A kit for practicing the method is also provided.

DEFINITIONS

Figure 1:
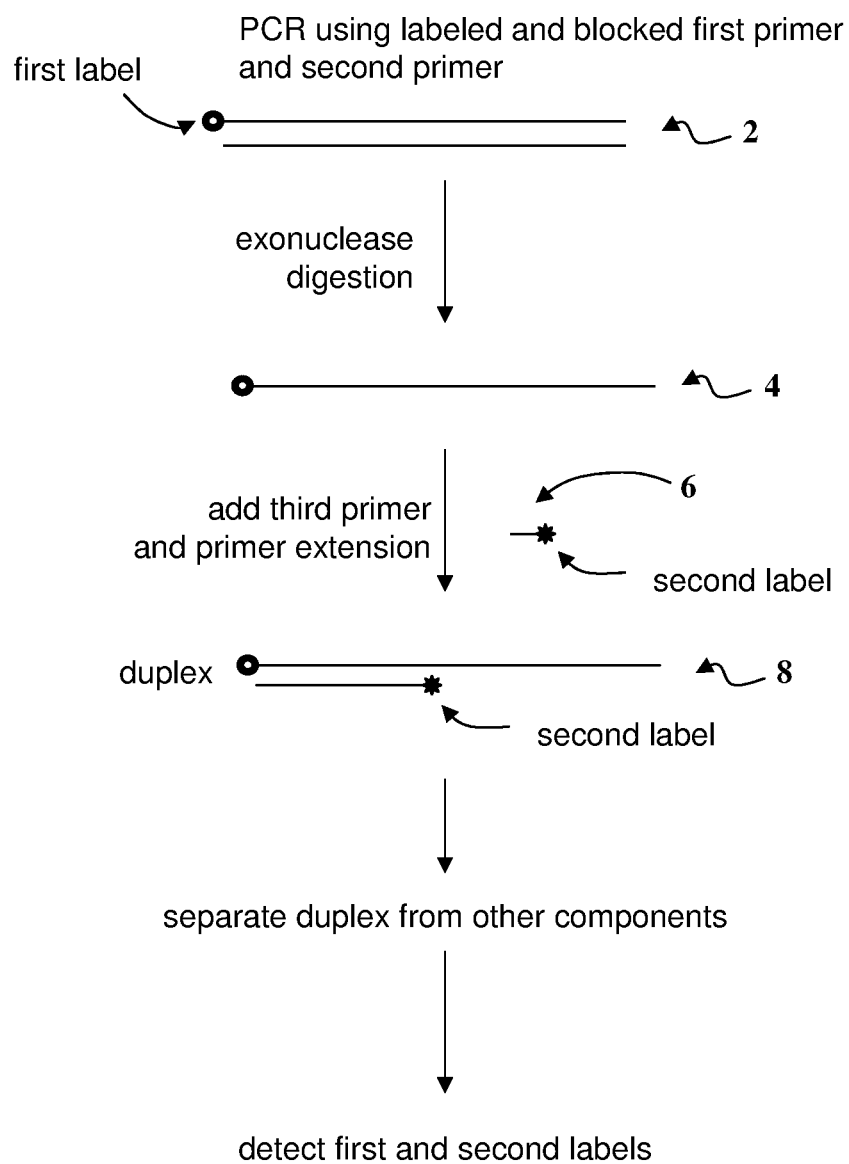
FIG. 1 schematically illustrates certain features of one embodiment of the subject method.

The term "sample" as used herein relates to a material or mixture of materials, typically, although not necessarily, in liquid form, containing one or more analytes of interest. A "nucleic acid sample" is a sample that contains nucleic acid. A sample may contain a single nucleic acid species. Certain samples contain at least 10, at least 10, at least 1,000, or more, e.g., at least 100,000 or at least 100,000 different species, e.g., different nucleic acid fragments or different sequences. A sample may be a biological sample from any source, e.g., a sample of cerebro-spinal fluid, lymph, blood, blood derivatives (e.g. sera), liquidized tissue, urine, fecal material, swab or nasal wash from a human, cell culture, or a foodstuff.

The term "genomic sample" as used herein relates to a material or mixture of materials, containing genetic material from an organism. The term "genomic DNA" as used herein refers to deoxyribonucleic acids that are obtained from an organism. The terms "genomic sample" and "genomic DNA" encompass genetic material that may have undergone amplification, purification, or fragmentation. The term "test genome," as used herein refers to genomic DNA that is of interest in a study.

The term "label" can be any detectable label, including a radioactive label and a non-radioactive label. Non-radioactive labels include optically detectable labels, including fluorescent labels and fluorescent barcodes, as well as mass tagged labels. A nucleic acid can be directly or indirectly labeled, where an indirectly labeled nucleic acid contains a ligand (e.g., biotin) for a label. A nucleic acid that is directly labeled is linked to the label covalently or non-covalently. Labels of interest include directly detectable and indirectly detectable non-radioactive labels such as fluorescent labels and mass tags.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleotides, e.g., can participate in Watson-Crick base pairing interactions. Naturally-occurring nucleotides include guanine, cytosine, adenine and thymine (G, C, A and T, respectively).

The term "oligonucleotide" as used herein denotes a single stranded multimer of nucleotide of from about 2 to 500 nucleotides. Oligonucleotides may be synthetic or may be made enzymatically, and, in some embodiments, are 10 to 50 nucleotides in length. Oligonucleotides may contain ribonucleotide monomers (i.e., may be oligoribonucleotides) or deoxyribonucleotide monomers. Oligonucleotides may be 10 to 20, 21 to 30, 31 to 40, 41 to 50, 51-60, 61 to 70, 71 to 80, 80 to 100, 100 to 150, 150 to 200 or greater than 200 nucleotides in length, for example.

The term "primer" as used herein refers to an oligonucleotide that has a nucleotide sequence that is complementary to a region of a target nucleic acid. A primer binds to the complementary region and is extended, using the target nucleic acid as the template, under primer extension conditions. A primer may be in the range of about 20 to about 60 nucleotides although primers outside of this length are envisioned. A "primer" can be extended from its 3' end by the action of a polymerase. An oligonucleotide that cannot be extended from its 3' end by the action of a polymerase is not a primer.

The term "primer extension conditions" as used herein refers to conditions suitable for the extension of a primer that is bound to a complementary region in a target nucleic acid. Primer extension conditions include incubating a duplex nucleic acid with nucleotides, a polymerase and a buffer for a period of time at a certain temperature. Such conditions are well known in the art. The resulting new strand produced by primer extension is referred herein as a "primer extension product."

The term "amplifying" as used herein refers to generating one or more copies of a target nucleic acid, using the target nucleic acid as a template.

A "polymerase chain reaction" or "PCR" is an enzymatic reaction in which a specific template DNA is amplified using one or more pairs of sequence specific primers.

"PCR conditions" are the conditions in which PCR is performed, and include the presence of reagents (e.g., nucleotides, buffer, polymerase, etc) as well as temperature cycling (e.g., through cycles of temperatures suitable for denaturation, renaturation and extension), as is known in the art.

A "multiplex polymerase chain reaction" or "multiplex PCR" is an enzymatic reaction that employs two or more primer pairs for different targets templates. If the target templates are present in the reaction, a multiplex polymerase chain reaction results in two or more amplified DNA products that are co-amplified in a single reaction using a corresponding number of sequence-specific primer pairs.

The term "sequence-specific primer" as used herein refers to a primer that only binds to and extends at a unique site in a sample under study. In certain embodiments, a "sequence-specific" oligonucleotide may hybridize to a complementary nucleotide sequence that is unique in a sample under study.

The term "complementary" as used herein refers to a nucleotide sequence that base-pairs by non-covalent bonds to a target nucleic acid of interest. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is fully complementary to a target of interest such that every nucleotide in the sequence is complementary to every nucleotide in the target nucleic acid in the corresponding positions. In certain cases, a nucleotide sequence may be partially complementary to a target, in which not all nucleotide is complementary to every nucleotide in the target nucleic acid in all the corresponding positions.

The term "probe," as used herein, refers to a nucleic acid that is complementary to a nucleotide sequence of interest. In certain cases, detection of a target analyte requires hybridization of a probe to a target. In certain embodiments, a probe may be immobilized on a surface of a substrate, where the substrate can have a variety of configurations, e.g., a sheet, bead, or other structure. In certain embodiments, a probe may be present on a surface of a planar support, e.g., in the form of an array.

The terms "determining", "measuring", "evaluating", "assessing", "analyzing", and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

As used herein, the term "$T_m$" refers to the melting temperature an oligonucleotide duplex at which half of the duplexes remain hybridized and half of the duplexes dissociate into single strands. The $T_m$ of an oligonucleotide duplex may be experimentally determined or calculated using the following formula $T_m$=81.5+16.6($\log_{10}$[$Na^+$])+ 0.41 (fraction G+C)−(60/N), where N is the chain length and [$Na^+$] is less than 1 M. See Sambrook and Russell (2001; Molecular Cloning: A Laboratory Manual, $3^{rd}$ ed., Cold Spring Harbor Press, Cold Spring Harbor N.Y., ch. 10).

As used herein, the term "$T_m$-matched" refers to a plurality of nucleic acid duplexes having $T_m$s that are within a defined range, e.g. ±5° C., ±10° C., or ±15° C.

The term "strand" as used herein refers to a nucleic acid made up of nucleotides covalently linked together by phosphodiester bonds. One strand of nucleic acid does not include nucleotides that are associated solely through hydrogen bonding, i.e., via base-pairing, although that strand may be base-paired with a complementary strand via hydrogen bonding.

A nucleic acid may exist in a single stranded or a double-stranded form. A double stranded nucleic acid has two complementary strands of nucleic acid may be referred to herein as the "first" and "second" strands or some other arbitrary designation. The first and second strands are distinct molecules, and the assignment of a strand as being a first or second strand is arbitrary and does not imply any particular orientation, function or structure. The nucleotide sequences of the first strand of several exemplary mammalian chromosomal regions (e.g., BACs, assemblies, chromosomes, etc.), as well as many pathogens, are known, and may be found in NCBI's Genbank database, for example. The second strand of a region is complementary to that region.

The term "one strand," as used herein, refers to either strand of a nucleic acid but not both strands of a nucleic acid. When an oligonucleotide or a primer binds or anneals "one strand" or an exonuclease degrades "one strand", it binds to or degrades only one strand but not the other. The term "the other strand," as used herein, refers to the strand that is complementary to the "one strand." When an oligonucleotide or a primer binds or anneals "to one strand," it binds to only one strand, e.g., the first or second strand, but not the other strand.

The term "complementary to sites in only one strand," as used herein, refers to complementarity to sites on only one strand but not the other strand of a reference nucleic acid.

The term "mixture", as used herein, refers to a combination of elements, that are interspersed and not in any particular order. A mixture is heterogeneous and not spatially separable into its different constituents. Examples of mixtures of elements include a number of different elements that are dissolved in the same aqueous solution. In other words, a mixture is not addressable. To be specific, an array of surface-bound polynucleotides, as is commonly known in the art and described below, is not a mixture of surface-bound polynucleotides because the species of surface-bound polynucleotides are spatially distinct and the array is addressable.

The term "partial duplex" refers to a DNA molecule containing a single stranded portion and a double stranded portion, as illustrated by element 8 in FIG. 1.

The term "separating" generally refers to the enrichment of a substance in a sample (e.g., double stranded reaction products) relative to selected components present in the sample. In certain cases, separating involves transferring the substance from a first vessel to a second vessel such that, in the second vessel, the substance is substantially free (e.g., at least 2%, at least 5%, at least 10%, at least 20%, at least 50%, or more, up to about 90% to 95% or more free) of a significant percent of a selected component present in the first vessel. In certain embodiments, a substantially purified component comprises at least at least 10%, at least 30%, at least 50%, at least 80%, or at least 90 to 95% or more of the sample, excluding water and other solvents. Techniques for separating nucleic acids are well-known in the art and include, for example, ion-exchange chromatography, affinity chromatography, size exclusion chromatography, precipitation and sedimentation according to density.

DESCRIPTION OF EXEMPLARY EMBODIMENTS

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Method of Sample Analysis

In the following description, the use of arbitrary designations to indicate different components of the subject method (e.g., "first", "second" and "third", and "forward" and "reverse") implies no order in which the components are used. Further, in the following description, the strand that is degraded, i.e., the "one strand", is arbitrarily designated as the bottom strand to be consistent with FIG. 1. As would be readily apparent, if the bottom strand of the double stranded PCR product is an extension product of the labeled primer (arbitrarily designated herein as the "second" primer) the "top" strand would be degraded. Both embodiments are envisioned.

FIG. 1 schematically illustrates certain features of the subject method. With reference to FIG. 1, certain embodiments of the method comprise: contacting a nucleic acid sample with a first primer and a second primer under PCR conditions to produce double stranded product 2, wherein the second primer comprises a first label, as shown in FIG. 1, and is 5' blocked. Next, double stranded product 2 is contacted with exonuclease to degrade one strand of the double-stranded product to produce single stranded product 4. The strand that is degraded is an extension product of the first primer. Single stranded product 4 is then contacted with third primer 6 under primer extension conditions, where third primer 6 comprises a second label as illustrated in FIG. 1. The second label is detectable independently from the first label. The contacting results in hybridization of third primer 6 to single stranded product 4 and extension of third primer 6 using the single stranded product as a template to produce partial duplex 8. The partial duplex is optionally separated from other components used in the reaction method (e.g., other single stranded nucleic acids such as unextended primers, etc.), and the first and second labels of the separated partial duplex are detected. Detection of the first and second labels indicates that a target nucleic acid is in the nucleic acid sample. In certain cases the first and second labels are optically distinguishable labels (e.g., different fluorophores) or they may contain moieties of detectably different mass (i.e., labeled with a mass tag). In embodiments in which mass tags are employed, the mass tags may be cleaved from the separated partial duplex, and subsequently detected by mass spectrometry.

As noted above, the first primer is extended during PCR to make a strand that is subsequently enzymatically degraded using an exonuclease. As such, the 5' end of the first primer and its extension product, when part of double stranded product 2, is a substrate for an exonuclease. In certain embodiments, the first primer may contain a 5' phosphate group, although other groups are compatible with the exonuclease used, and are not blocked (i.e., do not contain a nuclease-resistant nucleotide that blocks the action of the exonuclease used). In one embodiment, the first primer contains a 5' phosphate group and may be made up of only natural nucleotides (i.e., guanine, cytosine, adenine and thymine). The first primer may be unlabeled. As would be apparent, the 3' end of the first primer can be extended during PCR.

The second primer comprises a first label and is 5' blocked in that it contains a nuclease-resistant nucleotide at a position that is at or 5' the position of the first label, thereby protecting the extension product containing the first label from attack by the exonuclease. Examples of such nuclease resistant nucleotides include phosphorothionate nucleotides, although other nucleotides, e.g. a PNA nucleotide, or an oligonucleotide that does not contain a 5' phosphate group (e.g., an oligonucleotide that contains a 5' hydroxyl group) may be employed. In one embodiment, degradation of the extension product of the primer may be blocked by the label itself, i.e., using a labeled nucleotide, where the label of the labeled nucleotide blocks the exonuclease. For example, degradation of the extension product of the second primer may be blocked by the first label on the second primer, as will be described in greater detail below.

In addition the primers, exemplary reaction buffers and DNA polymerases used in the subject method include those described in, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y. Reaction buffers and DNA polymerases suitable for PCR may be purchased from a variety of suppliers, e.g., Invitrogen (Carlsbad, Calif.), Qiagen (Valencia, Calif.) and Stratagene (La Jolla, Calif.). Exemplary polymerases include Taq, Pfu, Pwo, UlTma and Vent, although many other polymerases may be employed in certain embodiments. Guidance for the reaction components suitable for use with a polymerase as well as suitable conditions for its use, is found in the literature supplied with the polymerase.

The PCR reaction contains a nucleic acid sample. The nucleic acid sample may contain genomic DNA or an amplified version thereof (e.g., genomic DNA amplified using the methods of Lage et al, Genome Res. 2003 13: 294-307 or published patent application US20040241658, for example), cDNA, or DNA from a pathogen-infected subject, or total DNA isolated from a biological sample, for example. In exemplary embodiments, the nucleic acid sample may contain a sample from human or plant that is expected to contain pathogen. Since, as will be described below, the method may be employed for diagnostic purposes, the nucleic acid of the nucleic acid sample may or may not contain target nucleic acid for the primers used.

After PCR, one strand of the double-stranded product is degraded by the action of an exonuclease that acts in the 5' to 3' direction and catalyzes the removal of 5' mononucleotides from duplex DNA. Lambda exonuclease and T7 exonuclease are examples of exonucleases that may be employed in the method, which enzymes may be purchased from such vendors as NEB (Ipswich, Mass.), EPICENTRE Biotechnologies (Madison, Wis.), Cambio Ltd. (Cambridge, UK) etc., and used in accordance with manufacturer's instructions. Lambda exonuclease is described in Subramanian, et al (Nucleic Acids Res 2003 31: 1585-1596) and Mitsis et al (Nucleic Acids Res. 1999 27: 3057-3063). Since the second primer is blocked and the first primer is not blocked, the exonuclease degrades one strand of the double stranded product (i.e., the extension product of the first primer), but not the other, to make single stranded product 4.

Third primer 6 is annealed with single stranded product 4, and extended under primer extension conditions. The polymerase used in the extension reaction may include but is not limited to any DNA-template dependent DNA polymerase, e.g., T4 DNA polymerase, Taq polymerase, the Klenow fragment of DNA polymerase I and the like), thermostable template-dependent polymerases (such as Pfu), or any combination thereof. As would be recognized by one of skill in the art, a wide variety of DNA polymerases employable in the subject methods are available. In one embodiment, the polymerase may be Pfu-fusion Exo (−), which is the exo-nuclease-deficient version of Pfu polymerase fused to a double-stranded DNA-binding domain. In certain cases, a Pfu clamp loader may be added to the reagent mix to increase the processivity of the polymerase.

As illustrated in FIG. 1, the resultant partial duplex comprises: a) a single stranded segment comprising a first label-distal region (i.e., a region that is downstream of the binding site of the third primer)) and b) a double stranded segment comprising: i. the extension product of the third primer and ii. a first-label proximal region (i.e., a region that is upstream of the binding site of the third primer). In certain cases, the double stranded segment is of at least 50 base pairs in length, e.g., at least 100 base pairs in length, at least 200 base pairs in length, up to at least 500 base pairs in length or at least 1,000 base pairs in length, or more. In certain cases, the PCR product may be at least 100 base pairs in length, at least 200 base pairs in length, at least 500 base pairs in length, or at least 1,000 base pairs in length, up to 2 kb or 3 kb in length, or more.

In certain cases, the primer extension conditions comprise primer annealing and polymerization at high temperature, which may avoid false priming. In another embodiment, the polymerase may be added after the primer is annealed to ensure that polymerization occurs only after annealing is complete. The polymerase may also be kept inactive in the same reaction vessel of the primer extension condition by photocaging either the polymerase or the primers. In another embodiment, the enzyme employed in the prior PCR reaction may have sufficient activity to perform this step. As such, in certain embodiments, no extra polymerase need be added. In other embodiments, more of the same polymerase as used in the PCR step of the method may be added for primer extension. In certain embodiments, this primer extension step may be repeated one or two or more times. As would be readily apparent, the third primer is designed to anneal to the single stranded product, and prime nucleic acid synthesis towards the 5' end of the single stranded product (i.e., in a 5' to 3' direction).

The first and second labels employed in the method may be any labels that are distinguishable from one another. Labels of interest include directly detectable and indirectly detectable non-radioactive labels such as fluoroscent dyes. Directly detectable labels are those labels that provide a directly detectable signal without interaction with one or more additional chemical agents. Examples of directly detectable labels include fluorescent labels. Indirectly detectable labels are those labels which interact with one or more additional members to provide a detectable signal. In this latter embodiment, the label is a member of a signal producing system that includes two or more chemical agents that work together to provide the detectable signal. Examples of indirectly detectable labels include biotin or digoxigenin, which can be detected by a suitable antibody coupled to a fluorochrome or enzyme, such as alkaline phosphatase. In many one embodiment, the label is a directly detectable label. Directly detectable labels of particular interest include fluorescent labels.

Fluorescent labels that find use in the subject invention include a fluorophore moiety. Specific fluorescent dyes of interest include: xanthene dyes, e.g. fluorescein and rhodamine dyes, such as fluorescein isothiocyanate (FITC), 6-carboxyfluorescein (commonly known by the abbreviations FAM and F),6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R),5-carboxyrhodamine-6G (R6G$^5$ or G$^5$), 6-carboxyrhodamine-6G (R6G$^6$ or G$^6$), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. Specific fluorophores of interest that are commonly used in subject applications include: Pyrene, Coumarin, Diethylaminocoumarin, FAM, Fluorescein Chlorotriazinyl, Fluorescein, R110, Eosin, JOE, R6G, Tetramethylrhodamine, TAMRA, Lissamine, ROX, Napthofluorescein, Texas Red, Napthofluorescein, Cy3, and Cy5, etc.

As mentioned above, the labels used in the subject methods are distinguishable, meaning that the labels can be independently detected and measured, even when the labels are mixed. In other words, the amounts of label present (e.g., the amount of fluorescence) for each of the labels are separately determinable, even when the labels are co-located (e.g., in the same tube or in the same duplex molecule or in the same feature of an array). Suitable distinguishable fluorescent label pairs useful in the subject methods include Cy-3 and Cy-5 (Amersham Inc., Piscataway, N.J.), Quasar 570 and Quasar 670 (Biosearch Technology, Novato Calif.), Alexafluor555 and Alexafluor647 (Molecular Probes, Eugene, Oreg.), BODIPY V-1002 and BODIPY V1005 (Molecular Probes, Eugene, Oreg.), POPO-3 and TOTO-3 (Molecular Probes, Eugene, Oreg.), and POPRO3 TOPRO3 (Molecular Probes, Eugene, Oreg.). Further suitable distinguishable detectable labels may be found in Kricka et al. (Ann Clin Biochem. 39:114-29, 2002). Optically coded microdots may also be employed. In these embodiments, the different labels may be directly observable by detecting fluorescence, for example.

In particular embodiments and as noted above, the primers may be mass tagged, i.e., linked to a moiety that is detectable by its mass. Such mass tags are described in U.S. Pat. Nos. 6,312,893, 6,623,928, 7,247,434, 6,027,890, 6,815,212, 6,613,508, 7,052,846, and 6,444,422, as well as a variety of publications, e.g, Dominguez et al (Journal of Clinical Virology 2008 43:219-222), Briese et al (Emerg. Infect. Dis. 2005 11:310-313), Lamson et al (J. Infect. Dis. 2006 194:1398-1402); Palacios et al (Emerg. Infect. Dis. 2006 12:692-695); Renwick et al (J. Infect Dis. 2007 196: 1754-60) and Haff et al (Nucleic Acids Res. 1997 25:3749-50), which patents are publications are incorporated by reference for disclosure of mass tags. In these embodiments, the mass tags may be cleaved from the partial duplex, by, for example, uv light, and analyzed by mass spectroscopy, methods for which are described in the references cited above.

In particular embodiments, all of the steps of the method prior to the separating step (i.e., the PCR step, the exonuclease step and the primer extension step) may be performed sequentially in the same vessel, e.g., the same tube by the sequential addition of reagents to the reaction after each step is done. In one embodiment, the reagents for the exonuclease step and the third primer may be combined together prior to addition to the products of the PCR step, such that the exonuclease and primer extension steps can be performed without the addition of further reagents to the reaction. In particular embodiments, since a single stranded product is employed, there is no snap-cooling (i.e., no step that includes heating to at least 94° C. immediately followed by cooling to a temperature of at or below 5° C., e.g., heating and placing on ice or dry ice) required between the PCR step and the primer extension step to facilitate annealing of the third primer.

Depending on the application, the $T_m$ of the third primer may be higher (e.g., at 5° C. to 15° C. higher or 8° C. to 12° C. higher) than that of the first and second primers, which are generally $T_m$ matched. Further, any of the primers (e.g., the first primer, the second primer or the third primer, or any combination thereof) may have a unique "barcode" sequence at its 5' end which does not anneal with the sample and contains a nucleotide sequence that uniquely identifies the primer or any extension product thereof. Such molecular barcodes are described in, for example, U.S. patent application publications US20090181375, US20070264642, US20060051798 and US20040101835.

In certain embodiments and as noted above, the partial duplex may be separated from other nucleic acid in the reaction (e.g., nucleic acid in the reaction that is not the partial duplex such as single stranded nucleic acid, unextended primers, etc.) by methods that are well known in the art (e.g., using size exclusion or affinity chromatograph or the like). Kits for the purification of PCR products, e.g., a GenElute™ PCR Clean-Up Kit (Sigma-Aldrich, St. Louis, Mo.), QIAquick PCR Purification Kit (Qiagen, Valencia, Calif.), NucleoFast Kit (Clontech, Mountain View, Calif.), High Pure PCR Product Purification Kit (Roche Diagnostics, Indianapolis, Ind.) and QuickClean 5M PCR Purification Kit (Genscript, Piscataway, N.J.), are well known and may be employed herein. The first and second labels of the separated partial duplex may be detected, thereby determining if the nucleic acid is in the sample.

As noted above, the method may be a multiplex assay that employs multiple pairs of first and second primers, where each second primer comprises a distinguishable first label (i.e. labels that are distinguishable from one another); and multiple third primers that anneal to PCR products produced by the first and second primers, and that also contain second labels that are distinguishable from one another and also distinguishable from the first labels. The second and third primers used in this assay contain labels that are distinguishable from one another. In this embodiment, detection of pairs of labels indicates whether a particular nucleic acid is in the sample.

Depending on the desired complexity, a multiplex assay may be designed to detect multiple nucleic acids in a sample by using multiple pairs of first and second primers, where each pair of primers is designed to amplify a different product, as well as a corresponding set of third primers where each of the third primers anneals to the strand produced by extension of the second primer of each primer pair. The initial multiplex PCR may contain at least 5 pairs of first and second primers, at least 10 pairs of first and second primers, at least 15 pairs of first and second primers, at least 20 pairs of first and second primers, at least 25 pairs of first and second primers, at least 30 pairs of first and second primers, up to 40 or 50 or more pairs of first and second primers, with each primer pair having a corresponding third primer.

As would be readily apparent, the above-described primer pairs may be designed using any one of a number of different programs specifically designed to design primer pairs for multiplex PCR methods. For example, the primer pairs may be designed using the methods of Yamada et al. (*PrimerStation: a highly specific multiplex genomic PCR primer design server for the human genome*. Nucleic Acids Res. 2006 34:W665-9), Lee et al. (*MultiPrimer: software for multiplex primer design*. Appl. Bioinformatics 2006 5:99-109), Vallone et al. (*AutoDimer: a screening tool for primer-dimer and hairpin structures*. Biotechniques. 2004 37:226-31), Rachlin et al. (*Computational tradeoffs in multiplex PCR assay design for SNP genotyping* BMC Genomics. 2005 6:102) or Gorelenkov et al. (*Set of novel tools for PCR primer design* Biotechniques. 2001 31: 1326-30). In one embodiment, methods using optimization approaches for graph theory methods may be employed. In these methods the task of designing an optimal primer set for multiplex PCR is translated into a graph theory problem. Nodes represent the different molecules to be amplified (such as genomic loci) and edges represent potential conflicts, including primer-dimer potential. An efficient coloring of such a graph represents an efficient multiplexing scheme for the original set of loci. Such methods are described in Lipson (Master's Thesis entitled "Optimization Problems in Design of Oligonucleotides for Hybridization-based Methods", Technion-Israel Institute of Technology, 2002), which is incorporated by reference in its entirety. In a particular embodiment, a plurality of primer pairs may be designed using a program.

Kits

Also provided by the subject invention are kits for practicing the subject method, as described above. The subject kit, which may be in the form of a larger containing smaller containers, contains a) a first primer; b) a second primer that comprises a first label and that is 5' blocked; c) a third primer that comprises a second label; d) reagents for performing a PCR reaction using the first and second primers (e.g., a polymerase, reagents for polymerization (e.g., a buffer, nucleotides, etc)); and e) an exonuclease that degrades PCR-generated extension products of the first primer; wherein the first and second primers, when employed in a PCR reaction using a first template, produce a double stranded product, one strand of which is degradable using the exonuclease to produce a single stranded product; and wherein the third primer, when employed in a primer extension reaction, hybridizes to the single stranded product and is extended using the single stranded product as a template. The kit may be adapted for multiplexing, in which case it may contain multiple first and second primer pairs, and multiple third primers, etc. Certain kits may also contain a reference sample to be employed as a control in the subject method.

The various components of the kit may be present may be each present in separate vessels, or combined in one or more vessels. For example, the first and second primers may be mixed with the PCR reagents of the kit, or the reagents may be in a different vessel relative to the first and second primers. The various components of the kit may be in solution, e.g., in aqueous solution which in certain cases may be frozen, or in dried form for example.

In addition to above-mentioned components, the subject kit may further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

In addition to the instructions, the kits may also include one or more control analyte mixtures, e.g., two or more control analytes for use in testing the kit.

Utility

The above described sample analysis method finds use in a variety of diagnostic, research and clinical applications, including detecting infectious microorganisms, whole-genome sequencing, forensic analysis, and high throughput genotyping. For example, the multiplex PCR reaction mixture and sample analysis methods find use in pathogen detection (see, e.g., Elnifro, et al. Clinical Microbiology Reviews, 13: 559 (2000)), paternity testing (see, e.g., Hidding and Schmitt, Forensic Sci. Int., 113: 47 (2000); Bauer et al., Int. J. Legal Med. 116: 39 (2002)), preimplantation genetic diagnosis (see, e.g., Ouhibi, et al., Curr Womens Health Rep. 1: 138 (2001)), microbial analysis in environmental and food samples (see, e.g., Rudi et al., Int J Food Microbiology, 78: 171 (2002)), and veterinary medicine (see, e.g., Zarlenga and Higgins, Vet Parasitol. 101: 215 (2001)), among others.

The above described method is useful for the analysis of biological samples. The term "biological sample", as used herein, refers to a sample obtained from an organism or from components (e.g., cells) of an organism. The sample may be of any biological tissue or fluid. In some cases, the sample will be a "clinical sample" which is a sample derived from a patient. Such samples include, but are not limited to, sputum, blood, blood cells (e.g., white cells), tissue or fine needle biopsy samples, feces, urine, peritoneal fluid, and pleural fluid, or cells there from. Biological samples may also include sections of tissues such as frozen sections taken for histological purposes. The subject method also finds use in determining the identity of microbes in water, sewage, air samples, food products, including animals, vegetables, seeds etc., soil samples, plant samples, microbial culture samples, cell culture samples, tissue culture samples, as well as in human medicine, veterinary medicine, agriculture, food science, bioterrorism, and industrial microbiology etc. The subject method allows identification of hard to culture microbes since culturing the microbes may not be necessary for practice of this method. Consequently, the subject method provides for a rapid detection of microbes in a sample with limited waiting period for culturing microbes.

In one embodiment, a plurality of different primer pairs, each primer pair designed to specifically amplify nucleic acid of a particular pathogen (e.g., a bacterium or virus) can be used, where the product of the assay indicates whether one or more of the pathogens are in the sample. Microbes that might be identified using the subject method, include but are not limited to: a plurality of species of Gram (+) bacteria, plurality of species of Gram (−) bacteria, a plurality of species of bacteria in the family Enterobacteriaceae, a plurality of species of bacteria in the genus *Enterococcus*, a plurality of species of bacteria in the genus *Staphylococcus*, and a plurality of species of bacteria in the genus *Campylobacter*, *Escherichia coli* (*E. coli*), *E. coli* of various strains such as, K12-MG1655, CFT073, O157:H7 EDL933, O157:H7 VT2-Sakai, etc., *Streptococcus pneumoniae*, *Pseudomonas aeruginosa*, *Staphylococcus aureus*, coagulase-negative staphylococci, a plurality of *Candida* species including *C. albicans*, *C. tropicalis*, *C. dubliniensis*, *C. viswanathii*, *C. parapsilosis*, *Klebsiella pneumoniae*, a plurality of *Mycobacterium* species such as *M. tuberculosis*, *M. bovis*, *M. bovis* BCG, *M. scrofulaceum*, *M. kansasii*, *M. chelonae*, *M. gordonae*, *M. ulcerans*, *M. genavense*, *M. xenoi*, *M. simiae*, *M. fortuitum*, *M. malmoense*, *M. celatum*, *M. haemophilum* and *M. africanum*, *Listeria* species, *Chlamydia* species, *Mycoplasma* species, *Salmonella* species, *Brucella* species, *Yersinia* species, etc. Thus, the subject method enables identification of microbes to the level of the genus, species, sub-species, serovar, strain or variant of the microbe.

The subject methods, compositions and kits are also useful in identifying multiple different microbes in a single sample, simultaneously. This multiplexing aspect of the subject method may offer the advantages of conserving time, reagents and sample size.

The subject multiplex PCR reaction mix may also be used to investigate entire genomes or sub-regions thereof, particularly for sequence variations, e.g., single nucleotide polymorphisms, or SNPs. For example, multiplex PCR has been used in the analysis of the relationship between genetic variation and phenotype by making use of polymorphic DNA markers. Common SNPs occur at an average frequency of more than 1 per kilobase in human genomic DNA. Some SNPs, particularly those in and around coding sequences, are the direct cause of therapeutically relevant phenotypic variants.

The subject multiplex PCR reaction mix may be employed to investigate a number of clinically important polymorphisms, for example, the apoE2/3/4 variants are associated with different relative risk of Alzheimer's and other diseases (see Cordor, et al., Science 261 (1993), and the SNPs associated with cystic fibrosis (see Mutat Res. 2005 573:195-204), as well as many cancers, diabetes, heart disease, hypercholesterolemia and inflammatory diseases, as well a number of hereditary diseases.

In other embodiments, the subject multiplex PCR reaction mixture may be employed to evaluate the abundance of a plurality of different RNA molecules in a sample. In these embodiments, a sample containing RNA, e.g., mRNA, is subjected to reverse transcriptase conditions to produce cDNA, and regions of the cDNA are amplified using a subject multiplex PCR reaction mixture. Such methods, termed "reverse transcriptase-polymerase chain reaction" or "RT-PCR" methods are generally well known in the art (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.).

Other assays of interest which may be practiced using the subject method include: genotyping, scanning of known and unknown mutation, gene discovery assays, differential gene expression analysis assays; nucleic acid sequencing assays, and the like. Patents and patent applications describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference.

The above described applications are merely representations of the numerous different applications for which the subject method of use are suited. In certain embodiments, the subject method includes a step of transmitting data from at least one of the detecting and deriving steps, as described above, to a remote location. By "remote location" is meant a location other than the location at which the array is present and hybridization occur. For example, a remote location could be another location (e.g., office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart. "Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc.

EXAMPLE

An experiment was performed to test whether the above described sample analysis method could be used to detect and identify specific pathogen (*Salmonella enterica* subsp. *enterica* serovar Typhimurium) nucleic acid in a sample. Fourteen first and second primer pairs were designed to specifically amplify 13 *Salmonella enterica* subsp. *enterica* targets and one internal control DNA sequence, if present. The 14 first primers were 5' modified with a phosphate (Integrated DNA Technologies) and the 14 second primers were 5' labeled with unique mass tags (Eurofin Operon/ Agilent Technologies). Also 5' labeled with unique mass tags, 14 third primers were constructed to complement internal sequence of the first primer extension products.

One microliter of *Salmonella enterica* subsp. *enterica* serovar Typhimurium genomic DNA (10 ng) was mixed with a 24 µl solution containing all 14 primer pairs (300 nM each), 1× Brilliant Multiplex Master Mix (600553, Stratagene/Agilent Technologies), and nuclease-free PCR-grade water. Another sample (no template control, NTC) was prepared in the same fashion but 1 µl water was added instead of genomic DNA. An initial denaturation of the samples was done at 95° C. for 10 minutes followed by 30 PCR cycles of 15 s at 95° C., 30 s at 59° C., and 30 s at 72° C. Each sample was then mixed with 25 µl of a solution (400 µM each dATP, dGTP, dCTP, and dTTP; 2× PicoMaxx buffer and 0.05 U/µl PicoMaxx polymerase (600420, Stratagene/ Agilent Technologies); 1.2× Lambda exonuclease buffer and 0.3 U/µl Lambda exonuclease (M0262S, New England Biolabs); 180 nM of each of the 14 mass tag labeled third primer (Eurofin Operon/Agilent Technologies); nuclease-free PCR-grade water). Each sample was then incubated for 6 min. at 37° C., 10 min at 95° C., 1 min at 69° C., and 3 min at 72° C. The resultant duplexes of each sample were then purified using a PCR purification kit (400773, Stratagene/Agilent Technologies), UV photocleaved, and analyzed by an Agilent 6120 SQ mass spectrometer (Agilent Technologies) in single ion monitoring mode. Results were extracted by ChemStation software (Agilent Technologies).

Figure 2:
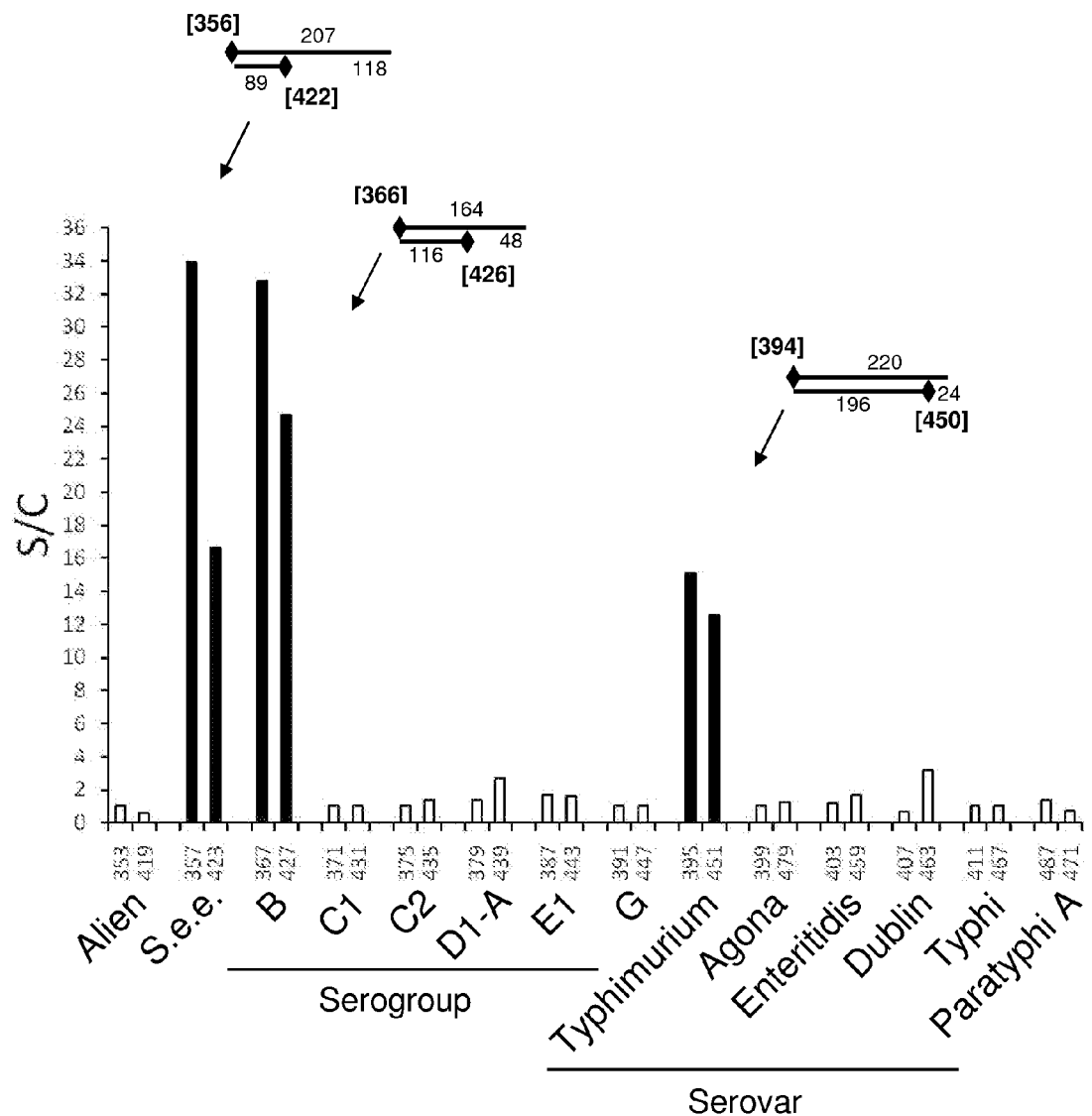
FIG. 2 is a graphical illustration of mass spectrometry data obtained by employing an embodiment of the subject method described designed to successfully identify variants of *Salmonella enterica* subsp. *enterica*. This embodiment is a 14-plex assay that tests for the presence of 13 different *Salmonella enterica* subsp. *enterica* nucleic acid targets in a sample by synthesizing duplexes which are dually labeled with mass tags using three primers, if the target is present. The primers for the 14$^{th}$ target, an non-hybridizing internal control, were included in the assay, but the non-hybridizing DNA was not added to the samples. The x-axis is labeled with each target name and above it the atomic mass unit of the two mass tags associated with each target's primers (left tag, second primer; right tag, third primer). The x-axis mass tag labels are expressed in terms of mass plus hydrogen (M+H)$^+$, the positive ion that is formed from the tag and detected by the mass spectrometer. The response of each tag measured in the spiked sample, divided by the negative control sample response for the identical tag, is shown above its (M+H)$^+$ value. Black-filled bars indicate a statistically significant response above background, and white-filled bars indicate responses which were not significantly above background. Depictions of the hybrid duplexes synthesized from the three positive targets are shown. The length of the entire hybrid is shown above the top strand of the hybrid and the length of the double-stranded and single-stranded segments of the hybrids is shown below their respective strand. Each hybrid is also shown with its associated labels (black diamonds) and the mass of each label (in brackets). S/C, sample response/control response. S.e.e., *Salmonella enterica* subsp. *enterica*. This graph empirically demonstrates that an embodiment of the subject method described can successfully identify specific nucleic acid targets in a sample by synthesizing from those targets duplexes which are dually labeled with mass tags. This experiment was performed in a multiplex fashion.

FIG. 2 depicts results from the mass spectrometry analysis of the purified samples. Only in the spiked sample were select mass tags, those which correspond to the three duplexes expected to be synthesized when *Salmonella enterica* subsp. *enterica* serovar Typhimurium genomic DNA is present in a sample, detected at significant levels. The three duplexes detected in the spike sample originate from the following nucleic acid targets: i) the 'S.e.e.' target, which identifies all variants of *Salmonella enterica* subsp. *enterica*. ii) the 'B' target, which identifies all variants of *Salmonella enterica* subsp. *enterica* who possess the serogroup B somantic antigen, serovar Typhimurium is a member of serogroup B. iii) the 'Typhimurium' target, which is intended to identify all strains of the serovar Typhimurium. Gel electrophoresis analysis of the samples showed that the three duplexes associated with Typhimurium detection were in fact formed in the sample spiked with Typhimurium, but absent in the no DNA control sample (data not shown). The mass tags associated with the primers in the reactions designed to amplify and detect targets of other variants of *Salmonella* were not detected at significant levels above background, which suggests that these primers did not synthesize any duplexes and that their target nucleic acid was absent from the sample.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of sample analysis comprising:
    a) contacting a nucleic acid sample with a first primer and a second primer under PCR conditions to produce a double stranded product, wherein said second primer comprises a first label and is 5' blocked;
    b) contacting said double stranded product with an exonuclease to degrade one strand of said double-stranded product to produce a single-stranded product, wherein said the strand that is degraded is an extension product of the first primer;
    c) contacting the single-stranded product with a third primer under primer extension conditions, wherein said third primer comprises a second label and wherein said contacting results in hybridization of the third primer to the single stranded product and extension thereof using said single stranded product as a template to produce a partial duplex that comprises a single stranded portion and a double stranded portion; and
    d) detecting the first and second labels of said partial duplex.

2. The method of claim 1, wherein said method comprises, between steps c) and d), separating said partial duplex from any single stranded nucleic acid.

3. The method of claim 1, wherein said second primer is 5' blocked by said first label.

4. The method of claim 1, wherein said partial duplex comprises: a) a single stranded segment region downstream of the binding site for the second primer; and b) a double stranded segment comprising: i. the extension product of said third primer and ii. a region upstream of the binding site for the second primer in said single stranded product.

5. The method of claim 1, wherein said double stranded segment is of at least 50 base pairs in length.

6. The method of claim 1, wherein said first and second labels are distinguishable fluorophores.

7. A method of sample analysis comprising:
    a) contacting a nucleic acid sample with a first primer and a second primer under PCR conditions to produce a double stranded product, wherein said second primer comprises a first mass tag and is 5' blocked;
    b) contacting said double stranded product with an exonuclease to degrade one strand of said double-stranded product to produce a single-stranded product, wherein said the strand that is degraded is an extension product of the first primer;
    c) contacting the single-stranded product with a third primer under primer extension conditions, wherein said third primer comprises a second mass tag that is distinguishable from the first mass tag and wherein said contacting results in hybridization of the third primer to the single stranded product and extension thereof using said single stranded product as a template to produce a partial duplex that comprises a single stranded portion and a double stranded portion; and
    d) detecting the first and second mass tags of said partial duplex.

8. The method of claim 7, wherein said method further comprises comprising cleaving the mass tags from said partial duplex to produce cleaved mass tags, prior to detection.

9. The method of claim 8, wherein the mass tags are cleaved from said partial duplex by ultra-violet light.

10. The method of claim 8, wherein said detecting comprises detecting the cleaved mass tags by mass spectrometry.

11. The method of claim 1, wherein steps a), b) and c) are performed sequentially in a single tube.

12. The method of claim 1, wherein said method is a multiplex assay that employs:
   multiple pairs of first and second primers, each second primer comprising a distinguishable first label; and
   multiple third primers comprising second labels that are distinguishable from one another and from said first labels.

13. The method of claim 12, wherein said multiplex assay produces multiple different partial duplexes that are separated other nucleic acid by chromatography prior to cleavage and subsequent detection of said first and second labels.

14. The method of claim 1, wherein said exonuclease is λ exonuclease.

15. The method of claim 1, wherein no snap-cooling is performed between steps a) and c) of said method.

16. The method of claim 1, wherein detection of the first and second labels indicates that said sample comprises a nucleic acid from a particular species.

* * * * *